(12) United States Patent  
Lee et al.

(10) Patent No.: US 8,498,717 B2  
(45) Date of Patent: Jul. 30, 2013

(54) NEURAL ELECTRONIC INTERFACE DEVICE FOR MOTOR AND SENSORY CONTROLS OF HUMAN BODY

(75) Inventors: Uhn Lee, Incheon (KR); Sang Hyouk Choi, Poquoson, VA (US)

(73) Assignee: Gachon University of Medicine & Science Industry-Academic Cooperation Foundation, Incheon (KR)

( * ) Notice: Subject to any disclaimer, the term of this patent is extended or adjusted under 35 U.S.C. 154(b) by 638 days.

(21) Appl. No.: 12/600,012

(22) PCT Filed: May 14, 2008

(86) PCT No.: PCT/KR2008/002662  
§ 371 (c)(1),  
(2), (4) Date: Jun. 22, 2010

(87) PCT Pub. No.: WO2008/140241  
PCT Pub. Date: Nov. 20, 2008

(65) Prior Publication Data  
US 2011/0022116 A1    Jan. 27, 2011

(30) Foreign Application Priority Data  
May 14, 2007 (KR) .................. 10-2007-0046435

(51) Int. Cl.  
*A61N 1/08* (2006.01)

(52) U.S. Cl.  
USPC ........................................... 607/61

(58) Field of Classification Search  
USPC .................. 607/45, 46, 48, 49, 61  
See application file for complete search history.

(56) References Cited

U.S. PATENT DOCUMENTS

| | | |
|---|---|---|
| 6,427,086 B1 | 7/2002 | Fischell et al. |
| 7,013,177 B1 | 3/2006 | Whitehurst et al. |
| 2002/0002390 A1* | 1/2002 | Fischell et al. .................. 607/45 |
| 2005/0187488 A1 | 8/2005 | Wolf |
| 2005/0283202 A1 | 12/2005 | Gellman |
| 2006/0149338 A1* | 7/2006 | Flaherty et al. .................. 607/49 |
| 2006/0184209 A1 | 8/2006 | John et al. |
| 2006/0212097 A1 | 9/2006 | Varadan et al. |

FOREIGN PATENT DOCUMENTS  
KR    10-2007-0005982 A    7/2002

OTHER PUBLICATIONS

International Search Report of International Application No. PCT/KR2008/002662, filed May 14, 2008, International Publication No. WO 2008/140241 A3, published Nov. 20, 2008, of Gachon University of Medicine # Science Industry-Academic Cooperation Foundation, of inventors Uhn Lee et al., for a Neural Electronic Interface Device for Motor and Sensory Controls of Human Body.

* cited by examiner

*Primary Examiner* — Tammie K Heller  
(74) *Attorney, Agent, or Firm* — Patent Office of Chung Park

(57) ABSTRACT

Provided is a neural electronic interface (NEI) device that includes: a deep brain monitoring and stimulation (DBMS) module that wirelessly receives power from a power transmitter at a hat put on a patient, monitors a state of a brain of the patient by collecting various signals of the brain through a probe pin device (PPD), and transmits the collected signals to a communicator of the hat, wherein a remote controller of the hat analyzes the collected signals and controls the DBMS through the controller to stimulate the brain.

16 Claims, 2 Drawing Sheets

NEURAL ELECTRONIC INTERFACE DEVICE FOR MOTOR AND SENSORY CONTROLS OF HUMAN BODY

CROSS REFERENCES TO RELATED APPLICATIONS

This application is a national phase application based upon priority International PCT Patent Application No. PCT/KR2008/002662 filed 14 May 2008, International Publication No. WO/2008/140241 A2 published 20 Nov. 2008, which is based upon priority Korean Patent Application No. 10-2007-0046435 filed 14 May 2007.

BACKGROUND OF THE INVENTION

1. Technical Field

The present invention relates to a neural electronic interface (NEI) device for motor and sensory controls of a human body, and more particularly, to a NEI device into which wireless technology, a smart micro-sensor, a nano probe pin device (PPD), etc. are integrated and which is implanted into a brain of a patient having motor and sensory problems in order to monitor activities of a cerebral nerve or stimulate the cranial nerve so as to normalize motor and sensory functions of the patient.

2. Background Art

People are exposed to accidents or diseases that may result in them losing the ability to function or move. There are limits to curing such patients in medical science. Medical and biological engineering in which an engineering field is grafted into a medical field has been developed in order to overcome the above-described limits. Thus, many areas of a health management system have been changed.

For example, cardiac pacemakers and defibrillators have saved lives of hundreds of people and cured heart diseases. Also, surgeons implant deep brain stimulation (DBS) devices into brains of patients to control abnormal brain functions of the patients using techniques of cardiac pacemakers.

Abnormal physical actions or mental disorders derive from abnormal functions of brains such as Parkinson's disease or an obsessive-compulsive disorder (OCD).

Parkinson's disease is a chronic degenerative disease whose main symptoms are shivering of hands and feet, slow actions, and hardening of muscles.

Neurosurgeons use DBS devices to cure health problems such as Parkinson's disease, OCD, and hypochondria. Such a DBS device applies current pulses to a cerebral nerve through electrodes, which are implanted into the cerebral nerve, in order to stop shivering, which is a main symptom of a disease, and relax stooped muscles.

A method using a DBS is a surgical method for curing an OCD and is effective in curing Parkinson's disease.

Operations using DBS devices have been performed since Alim-Louis Benabid in the Grenoble University Hospital of France reported on 80 or more Parkinson's disease patients in 1993. Thus, about thirty thousand similar operations have been very successfully performed throughout the world.

FIG. 1 illustrates a conventional DBS device which is implanted into a human body. As shown in FIG. 1, the conventional DBS device includes an electrode needle 546 and a power supply unit 560. The electrode needle 546 is implanted into a position of a cerebral nerve to provide an electric stimulation to the cerebral nerve so as to restore an abnormal function of a brain to a normal state. The power supply unit 560 is connected to the electrode needle 546 through an electric wire 550 to supply power to the electrode needle 546.

The DBS device having the above-described structure is prominently effective in curing a Parkinson's disease or an OCD. Also, the DBS device sews the power supply unit 560 having a power source such as a battery into abdomen or thorax and is turned on or off by remote control using a skin. Thus, the DBS is clinically simply used.

However, a process of implanting an electrode, which inhibits or stimulates a predetermined part of a cerebral nerve, into a deep part of a brain is required to normalize a function of the brain of a patient so as to adopt the DBS device. Also, when the DBS device uses an electric wire in a human body to supply power, transmit data, and program software, a plurality of problems occur.

In other words, since the implantation of the power source or the electric wire into a body of a patient is complicated, the DBS device provides the inconvenience to the patient. Also, if the electric wire 550 installed underneath a skin of the patient short-circuits or power of the battery installed in the abdomen or thorax is consumed, a surgical operation is repeatedly performed to replace or repair a corresponding part.

An inexpensive electroencephalogram (EEG) represents common electric activities of millions of nerves distributed in a wide area of the cerebral cortex but does not supply a time-varying activity control signal, which is required for a specific part of a human body, in real time. In other words, brain activities must be observed and cured in an accurate problematic position in order to cure brain dysfunctions which are generally developed in patients. However, a device for solving this problem has not been developed.

BRIEF SUMMARY OF THE INVENTION

Disclosure of Invention Technical Problem

The present invention provides a neural electronic interface (NEI) device into which wireless technology, a smart micro-sensor, and a nano probe pin device (PPD) are integrated in order to monitor chemical and/or physical information of a brain, auto-nomically alleviate or cure abnormal functions of a cerebral nervous system, and monitor or stimulate the brain of a patient using power wirelessly supplied from an outside of a body of the patient so as to stably provide a deep brain stimulation (DBS) cure without replacing or repairing a power source.

Advantageous Effects

A neural electronic interface (NEI) device for motor and sensory controls of a human body according to the present invention realizes a wireless deep brain stimulation (DBS) device to normalize an abnormal function of a cerebral nervous system of a patient. The NEI device also strengthens a weakened function of the cerebral nervous system and alleviates a pain of the patient during an operation using the DBS device. In addition, the NEI device monitors a function of a brain of the patient and controls nerves using a stimulation signal and a feedback signal which are transmitted through a wireless interface. Thus, the NEI device directly and immediately cures a nervous system-related disease of the patient.

A more detailed explanation of the invention is provided in the following detailed description and appended claims taken in conjunction with the accompanying drawings.

DETAILED DESCRIPTION OF THE INVENTION

The following is a detailed description and explanation of the preferred embodiments of the invention and best mode for practicing the invention.

Best Mode for Carrying Out the Invention

According to an aspect of the present invention, there is provided a neural electronic interface (NEI) device including: a deep brain monitoring and stimulation (DBMS) module which is implanted through a skull under a scalp to contact the cerebral nerve of the patient; and a hat module which is installed at a hat put on a head of the patient, wirelessly supplies power to the DBMS module, and performs a wireless communication with the DBMS module to transmit a control signal to control the DBMS module according to nervous system data which is monitored and fed back from the DBMS module.

Mode for the Invention

The present invention synthesizes several scientific fields including materials science, micro-electromechanical systems (MEMS), neuroscience, neurosurgery, particularly, motor and sensory controls, etc. in order to solve problems related to functional electrical stimulation (PES) and neural electronic interface (NEI).

Exemplary embodiments of the present invention will now be described in detail with reference to the attached drawings.

Figure 1:
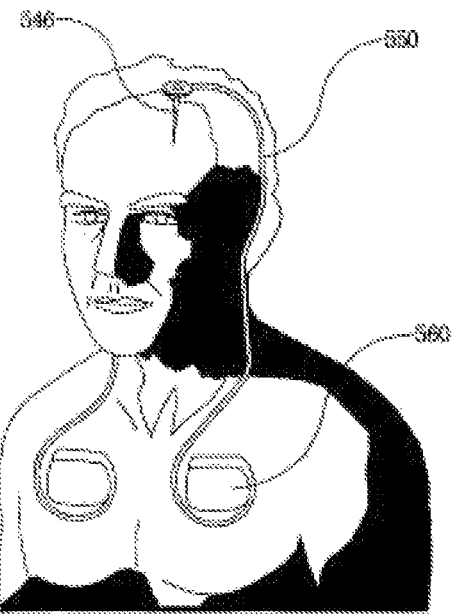
FIG. 1 illustrates a conventional deep brain stimulation (DBS) device which is implanted into a human body.
Figure 2:
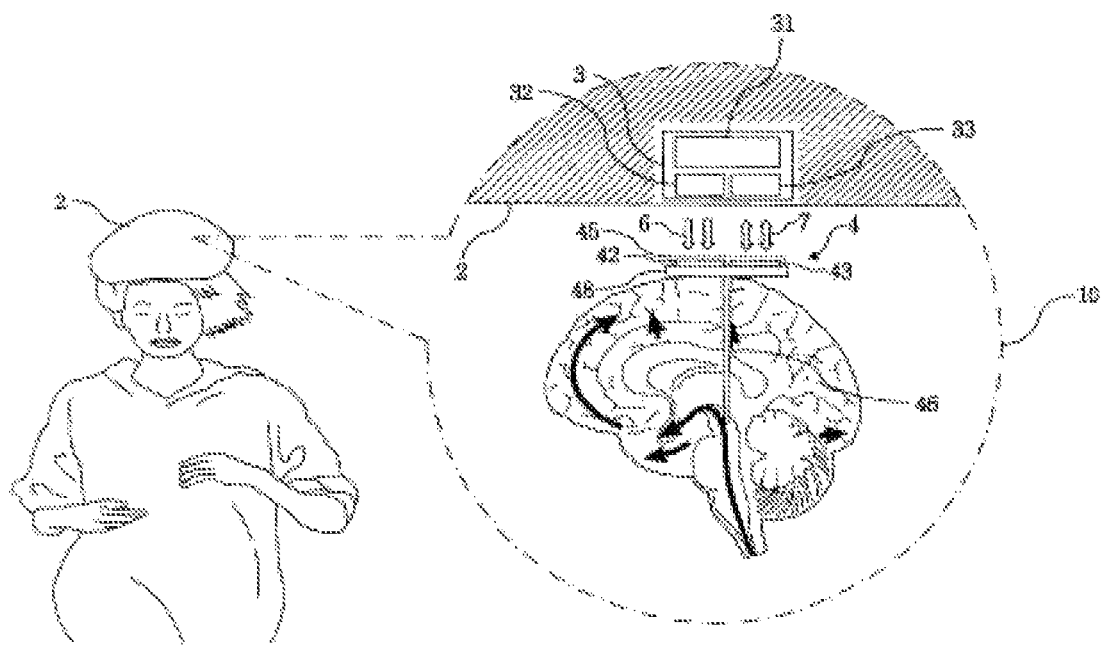
FIG. 2 illustrates a neural electronic interface (NEI) device for motor and sensory controls of a human body according to an embodiment of the present invention.

FIG. 2 illustrates a NEI device for motor and sensory controls of a human body according to an embodiment of the present invention. Referring to FIG. 2, a NEI device 10 of the present embodiment controls motor and sensory functions using nanotechnology and includes a deep brain monitoring and stimulation (DBMS) module 4 and a hat module 3. The DBMS module 4 is implanted into a brain of a patient, and the hat module 3 is put on a head of the patient to perform wireless communications with the DBMS module 4.

The DBMS module 4 includes a probe pin device (PPD) 46 and a power and signal processor 45. The PPD 46 is implanted through a skull under a scalp to contact a deep cerebral nerve and monitors a nervous system of a patient or provides an electric stimulation to the nervous system. The power and signal processor 45 wirelessly receives power from the hat module 3 to drive the PPD 46 and performs wireless communications with the hat module 3.

The power and signal processor 45 includes a DBMS communicator 43 which wirelessly transmits and receives a data signal 7 and a power receiver 42 which wirelessly receives power 6 from the hat module 3. The power and signal processor 45 further includes a thin film 48 which is formed of a flexible material and fixed to a skull under a scalp so that parts of the power and signal processor 45 including the DBMS 43 and the power receiver 42 are installed thereon. The PPD 46 is connected to a center of a lower surface of the thin film 48 to be fixed to a position in which nerves are to be stimulated.

Here, the DBMS communicator 43 receives a command signal from the hat module 3 or transmits a sensor signal, which is measured by the PPD 46, to the hat module 3.

The hat module 3 includes a power transmitter 32, a communicator 33, and a remote controller 31. The power transmitter 32 wirelessly supplies power necessary for driving the DBMS module 4. The communicator 33 performs communications with the DBMS communicator 43. The remote controller 31 is connected to the communicator 33 to receive the sensor signal measured by the PPD 46 and transmit a control signal for the sensor signal.

The power transmitter 32 of the hat module 3 and the power receiver 42 of the DBMS module 4 constitute a wireless power transmission module to wirelessly transmit power so as to supply power for providing an electric stimulation to the nervous system of the patient without installing an additional power source in a body of the patient.

A power transmission method of the wireless power transmission module may be a power transmission method using induced power or an electric wave transmission method using microwaves.

In the power transmission method using the induced power, the power transmitter 32 includes a rotating magnetic field disc, and the power receiver 42 includes an induction coil which is combined with a rotating magnetic field. Thus, induced power is generated using a relative motion between the rotating magnetic field disc and the induction coil.

In the electric wave transmission method using the microwaves, the power transmitter 32 includes a microwave antenna which transmits microwaves like a horn antenna, and the power receiver 42 includes a rectenna which receives microwaves and transforms the microwaves into power. Thus, power energy is transmitted from the outside into a human body using microwaves.

The power transmission method using the induced power and the electric wave transmission method using the microwaves are disclosed in Korean Patent Application Nos. 2007-0046408 (Deep Brain Stimulation (DBS) device Driven by Power Wirelessly Supplied by Magnetic Induction) and 2007-0046404 (Wireless Power Transmission Deep Brain Stimulation (DBS) device) which have been applied by the present applicant.

The NEI device 10 of the present embodiment is implanted into the brain of the patient having a problem in the nervous system to monitor variations in the cerebral nerve through a wireless interface which is installed between the DBMS module 4 and the hat module 3. If an arm 1 of the patient is abnormally moved, the NEI device 10 controls the PPD 46 of the DBMS module 4 through the remote controller 32 of the hat module 3 to restore abnormal motor and sensory functions of the patient to normal states.

In other words, the NEI device 10 wirelessly supplies power to control a function of the brain of the patient and continuously monitors states of nerves. The NEI device 10 also wirelessly transmits monitored data to a control system which is installed outside a human body. In addition, the NEI device 10 controls a cerebral nerve stimulation function based on analyzed and processed feedback data to compensate for nervous abnormalities related to motor and sensory.

Figure 3:
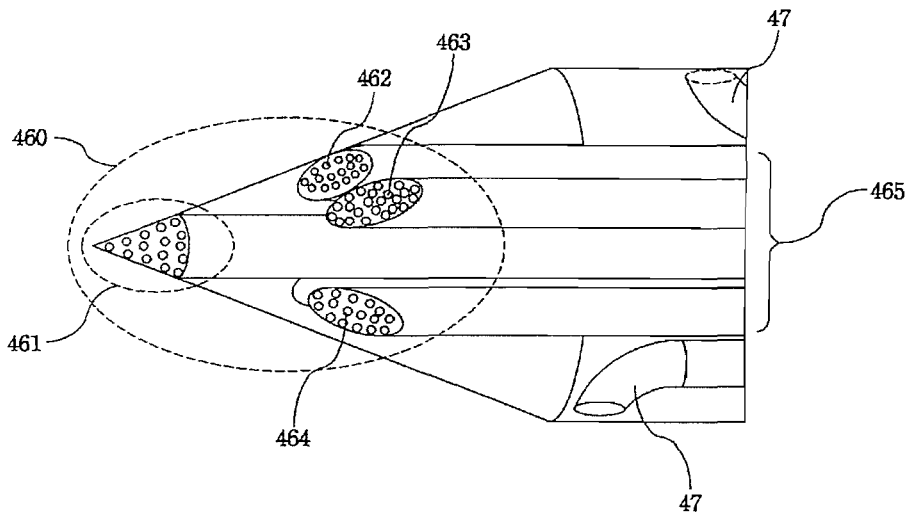
FIG. 3 illustrates a detailed structure of a probe pin device (PPD) of FIG. 2.

FIG. 3 illustrates the PPD 46 of FIG. 2. Referring to FIG. 3, the PPD 46 includes a sensor 460, a plurality of signal lines 465, and a plurality of stimulation electrodes 47. The sensor 460 includes a tip to sense a state of a brain tissue. The signal lines 465 are installed along a longitudinal direction of a body of the PPD 46 to transmit a signal sensed by the sensor 46 to the power and signal processor 45. The electrodes 47 transmit a voltage for stimulating a nerve cell.

Various signals monitored through the sensor 460 of the PPD 46 are wirelessly transmitted to the communicator 33 of the hat module 33 through the DBMS communicator 43 of the power and signal processor 45. Thus, the PPD 46 may be referred to as a wireless buried nerve probe.

The signal lines 465 each have a micro-diameter and extend from the power and signal processor 45 up to the tip of the PPD 46 along an interior of the PPD 46. The signal lines 465 are formed of a quartz optical fiber, gold lines, or platinum rods to transmit signals output from the sensor 460. A nano-sensor array including a voltage sensor 461, a chemistry sensor 462, a pressure sensor 463, and a temperature sensor 464 is integrated at ends of the signal lines 465 to constitute the sensor 460. Here, the voltage sensor 461, the chemistry sensor 462, the pressure sensor 463, and the temperature sensor 464 are exposed toward the brain tissue to respectively detect a voltage in a brain, a brain disease-related neurotransmitter (hereinafter referred to as a brain disease inducer), a brain pressure, and a brain temperature.

The pressure sensor 463 for measuring the brain pressure includes micro-nano elements and thus outputs an electric signal according to stress variations generated by the brain pressure.

The chemistry sensor 462 for detecting the brain disease inducer includes quantum dots which are formed at the ends of the signal lines 465 and each have a diameter between 5 nm and 20 nm. In order to detect the brain disease inducer, the chemistry sensor 462 senses variations of a fluorescence spectrum or a fluorescence resonance energy transfer (FRET) using fluorescence characteristics of the quantum dots which vary with interactions among the quantum dots occurring when the quantum dots are exposed to the brain disease inducer. A quantum dot-based sensor is mainly used in the biochemistry field and may be designed to interact with cells and tissues on a molecular level. The quantum dot-based sensor induces nerve protrusions to be grown on the quantum dots in order to connect the signal lines 465 to neurons of a cerebral cortex area. The chemistry sensor 462 of nano unit, which applies a nervous system, effectively transmits a neuron level signal, which is detected in the brain, to an external device.

The PPD 46 having the above-described structure is implanted into a minute path of an activity cerebral cortex so that a lower part of the PPD 46 contacts a deep cerebral nerve. Thus, a body of the PPD 46 may be formed of a material which does not react to and reject fluid in a human body. In particular, the body of the PPD 46 may be formed of a polymer or ceramic material which is physiologically well adapted to the human body. An insulating material is coated on a surface and the tip of the PPD 46, and the stimulation electrodes 47 of the PPD 46 are formed of insulator-coated gold lines.

Figure 4:
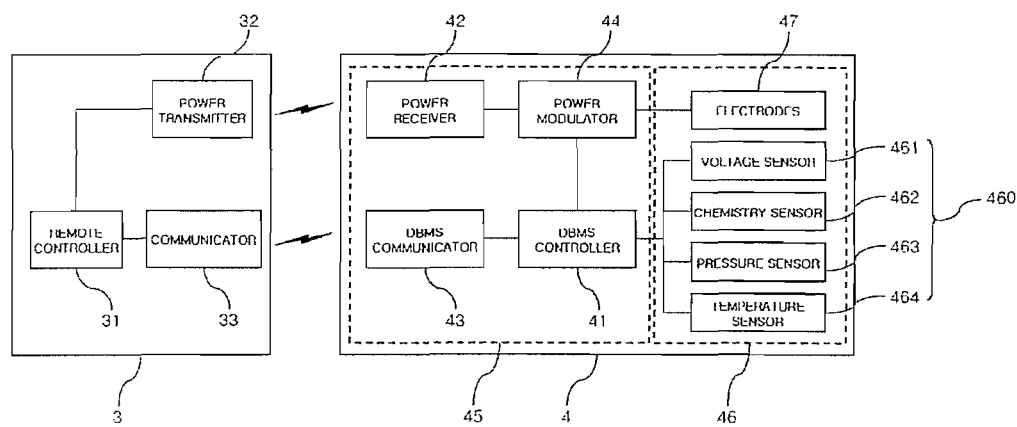
FIG. 4 is a block diagram of the NEI device of FIG. 2.

FIG. 4 is a block diagram of the NEI device of FIG. 2. A structure and an operation of the NEI device 10 will now be described in detail with reference to FIG. 4.

As previously described, the NEI device 10 includes the hat module 3 on which a patient is put and the DBMS module 4 which is implanted into a brain of the patient.

The hat module 3 includes the power transmitter 32 which wirelessly transmits the power, the communicator 33 which performs the wireless communications with the DBMS module 4, and the remote controller 31. The remote controller 31 controls a power transmission function of the power transmitter 32 and receives the data signal, which is collected and transmitted from the sensor 460 of the PPD 46 of the DBMS module 4, from the communicator 33. Next, the remote controller 31 analyzes and processes the data signal and transmits the command signal, which is to control a cerebral nerve stimulation function, to the DBMS module 4 through the communicator 33.

Here, the remote controller 31 analyzes the data signal, which is collected and transmitted from the sensor 460, in real time to determine that motor and sensory functions of the brain have entered abnormal states if the data signal seriously or abruptly fluctuates or have a shock waveform. The remote controller 31 immediately controls the power transmitter 32 to increase the wireless power transmitted to the DBMS module 4 so as to transmit power enough to stimulate a cerebral nerve. The remote controller 31 also analyzes a data signal, which is transmitted for a predetermined time section, using a lookup table, which is experimentally written, in order to determine an abnormal state of the brain. Here, output patterns of sensor signals for a patient having an abnormal brain function may be pre-written to write the lookup table.

The remote controller 31 transmits a command signal, which is to control a detection period of the sensor 460, to the power and signal processor 45 of the DBMS module 4 through the communicator 33 according to the analysis result. In other words, if the motor and sensory functions of the brain are in normal states, the remote controller 31 extends the detection period of the sensor 460 to reduce power consumed by the DBMS module 4. If the motor and sensory functions of the brain are in abnormal states, the remote controller 31 shortens the detection period of the sensor 460 to perform a fast feedback control for the abnormal states.

The remote controller 31 analyzes variation patterns of the data signal, which is transmitted from the sensor 460 for the predetermined time section, using a predetermined algorithm or the lookup table. Next, the remote controller 31 controls a power transmission function or a monitoring function according to the analysis result in order to restore the abnormal states of the motor and sensory functions to normal states.

The DBMS module 4, which is implanted into the brain, includes the PPD 46 which includes the sensor 460 and the stimulation electrodes 47 and the power and signal processor 45 which receives and modulates wirelessly transmitted power and processes a command signal and a feedback signal.

The sensor 460 includes the voltage sensor 461, the chemistry sensor 462, the pressure sensor 463, and the temperature sensor 464 which are installed at the tip of the PPD 46, to supply sensed various types of signals to the power and signal processor 45. The stimulation electrodes 47 transmit the cerebral nerve stimulation signal to inhibit the abnormal motor or sensory function of the patient.

The power and signal processor 45 includes the power receiver 42, a power modulator 44, a DBMS controller 41, and the DBMS communicator 43. The power receiver 42 wirelessly receives the power from the power transmitter 32 of the hat module 3. The power modulator 44 modulates the power enough to be used by the whole circuit, the PPD 46, etc. The DBMS controller 41 analyzes the monitoring signal transmitted from the PPD 46 and controls the power modulator 44 based on the analyzed monitoring signal. The DBMS communicator 43 transmits a signal measured by the sensor 460 to the remote controller 31 of the hat module 3 installed outside a scalp and receives a control command signal from the remote controller 31.

The DBMS controller 41 directly receives a sensor signal from the sensor 460 and deciphers the sensor signal. If a numerical value of each of the voltage, the brain disease inducer, the brain pressure, and the brain temperature respectively transmitted from the voltage sensor 461, the chemistry sensor 462, the pressure sensor 463, and the temperature sensor 464 exceeds a set normal range, the DBMS controller 41 operates the power modulator 44 to transmit a pulse voltage for stimulating a cerebral nerve through the stimulation electrodes 47. Here, power required for deep brain stimulation (DBS) may be a pulse wave having a pulse width between 60 μsec and 500 μsec in a minimum frequency of 200 Hz and may have a magnitude between 0V and ±10V. Therefore, the power modulator 44 modulates the power transmitted from the power transmitter 32 into a pulse wave, which has a magnitude between 0V and ±10, a frequency of 200 Hz, and a pulse width between 60 μsec and 500 μsec, and then supplies the pulse wave to the stimulation electrodes 47. Here, the DBMS controller 41 includes a synchronous sample/hold (SSH) module (not shown) to transform an analog signal output from the sensor 460 into a digital signal and transmit the digital signal to the DBMS communicator 43. A feedback signal input from the sensor 460 provides accurate information about chemical changes and nerve-electricity in the brain is supplied to the DBMS controller 41 and the remote controller 31 of the hat module 3. Here, the chemical changes and the nerve-electricity are related to motor. Thus, the NEI device 10 includes a total sensory feedback element which is self-operated by power which is wirelessly supplied.

In other words, the DBMS controller 41 of the DBMS module 4 controls the power modulator 44 according to a range of the transmitted feedback signal to control pulse power supplied to the stimulation electrodes 47 so as to perform a relatively simple, immediate management, i.e., a real-time control function, with respect to an abnormal state of a cerebral nervous system. The remote controller 31 of the hat module 3 controls the power transmission function or the monitoring function according to analysis results of variation types of a feedback signal which is transmitted within a predetermined time section. Thus, the remote controller 31 performs a complex, difficult control function which requires an analysis of data transmitted within a predetermined time section.

Accordingly, a NEI device according to the present invention is adopted in an activity cerebral cortex of a human brain to read and control motions of hands and feet of a patient so as to assist the patient in restoring abnormal activities. In other words, the NEI device detects an electric signal from a brain and feeds the electric signal back to the DBMS controller 41 having an algorithm determining a state of a patient and the remote controller 31 in order to determine whether a nervous function is in a normal state. If the nervous function is in an abnormal state, the NEI device wirelessly supplies power enough to stimulate the brain and drives the power modulator 44 to supply pulse power to the stimulation electrodes 47. Therefore, the NEI device corrects muscle shivering in real time using a feedback error correction algorithm, etc.

Also, compared to a conventional DBS device which is sewed into abdomen or thorax to be turned on or off by remote control through a skin, the NEI device 10 wirelessly transmits power. Thus, the NEI device 10 does not requires a surgical operation which is performed to replace a battery and other elements of the NEI device 10 which are implanted into a cell tissue of a patient.

Figure 5:
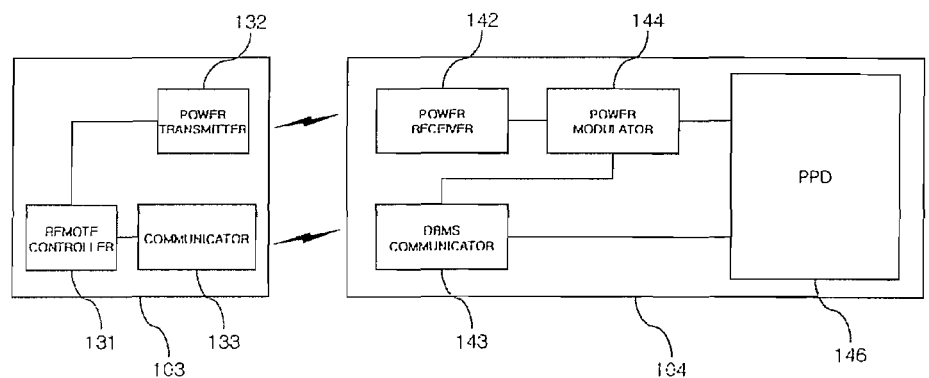
FIG. 5 is a block diagram of a NEI device for motor and sensory controls of a human body according to another embodiment of the present invention.

FIG. 5 is a block diagram of a NEI device for motor and sensory controls of a human body according to another embodiment of the present invention. Referring to FIG. 5, the NEI device of the present embodiment does not include the DBMS controller 41 of the DBMS module 4 and thus has a simpler structure than the NEI device 10 of the previous embodiment. Therefore, the NEI device of the present embodiment executes a control algorithm for normalizing functions of a brain using only the remote controller 31 of the hat module 3.

In other words, a remote controller 131 of a hat module 103 analyzes a data signal, which is transmitted from each sensor of a PPD 146 through a DBMS communicator 143 and a communicator 133, in real time. If the remote controller 131 determines that motor and sensory functions of a brain have entered abnormal states, the remote controller 131 controls a power transmitter 132 to increase wireless power transmitted to a power receiver 142 of a DBMS module 104 so as to transmit power enough to stimulate a cerebral nerve. The remote controller 131 simultaneously transmits a command signal to drive a power modulator 144, i.e., a counter signal, through the communicator 133. The power modulator 144 receives the counter signal through the DBMS communicator 143 and generates pulse power for stimulating the brain in order to normalize functions of the brain. Here, a sensor control module (not shown) is additionally installed to trigger and control each sensor of the DBMS module 104. Also, a command signal to modulate a detection period of a sensor 460 is transmitted to the sensor control module through the communicator 133 according to the analysis result of the remote controller 131. While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

A NEI device according to the present invention may be applied to a medical DBS device which monitors functions of a brain and controls nerves using a stimulation signal and a feedback signal transmitted through a wireless interface in order to directly and immediately cure a nervous disease of a patient.

Although embodiments of the invention have been shown and described, it is to be understood that various modifications, substitutions, and rearrangements of parts, components, and/or process (method) steps, as well as other uses of the neural electronic interface (NEI) device, can be made by those skilled in the art without departing from the novel spirit and scope of this invention.

What is claimed is:

1. A neural network interface (NEI) device for stimulating a cerebral nerve of a patient to control abnormal motor and sensory functions of a brain of the patient, the NEI device comprising:
   a hat module configured for placement over a head of the patient, wherein the hat module is configured to wirelessly supply power; and
   a deep brain monitoring and stimulation (DBMS) module including:
      a thin film configured to be fixed between a skull and a scalp of the patient; a probe pin device (PPD) having a shape of a pin, having a head portion that is directly attached to a lower surface of the thin film, and configured to be implanted through the skull under the scalp of the patient to thereby contact the cerebral nerve of the patient; and
      a power and signal processor disposed on the thin film and configured to wirelessly receive the power from the hat module, wirelessly transmit nervous system data monitored by the PPD to the hat module, and wirelessly receive a control command signal from the hat module to thereby control the DBMS module according to the nervous system data;

wherein:
(a) the hat module is configured to generate a rotating magnetic field toward the DBMS module and the DBMS module is configured to be driven using induced power which is generated by a magnetic induction which is generated by the rotating magnetic field; or
(b) the hat module is configured to transmit a microwave to the DBMS module and the DBMS module is configured to receive the microwave, transform the microwave into direct current (DC) power, and be driven by the DC power.

2. The NEI device of claim 1, wherein:
the DBMS module is configured to control pulse power for stimulating a nervous system according to a range of the nervous system data and to output the pulse power to the cerebral nerve; and
the hat module is configured to control the power transmitted to the DBMS module according to the nervous system data and control a monitoring period of the DBMS module.

3. The NEI device of claim 1, wherein the PPD comprises:
a sensor which is installed at a tip of the PPD and configured to sense a state of a brain tissue;
a plurality of signal lines embedded within the PPD and configured to transmit a signal detected by the sensor to the power and signal processor; and
a plurality of stimulation electrodes configured to transmit a voltage for stimulating a nervous cell.

4. The NEI device of claim 3, wherein the signal lines are formed of one of a quartz optical fiber, gold lines, and platinum rods.

5. The NEI device of claim 3, wherein the sensor is formed of at least one or combinations of a voltage sensor, a chemistry sensor, a pressure sensor, and a temperature sensor, wherein the voltage sensor detects a voltage in the brain, the chemistry sensor detects a brain disease inducer, the pressure sensor detects a brain pressure, and the temperature sensor detects a brain temperature.

6. The NEI device of claim 5, wherein the chemistry sensor is formed of quantum dots which are formed at the ends of the signal lines to detect the brain disease inducer using fluorescence characteristics of the quantum dots which vary with interactions among the quantum dots occurring when the quantum dots are exposed to the brain disease inducer.

7. The NEI device of claim 6, wherein the chemistry sensor is configured to induce nerve protrusions to be grown on the quantum dots to thereby improve electrical connections to neurons of a cerebral cortex.

8. The NEI device of claim 3, wherein the sensor is an integrated nano-sensor array.

9. The NEI device of claim 1, wherein the body of the PPD is formed of one of a polymer material and a ceramic material, and an insulating material is coated on a surface and a tip of the PPD.

10. The NEI device of claim 1, wherein the power and signal processor comprises:
a power receiver configured to wirelessly receive the power from the hat module;
a power modulator configured to modulate the power into power to drive the PPD;
a DBMS controller configured to control the power modulator according to a monitoring signal transmitted from the PPD; and
a DBMS communicator configured to transmit data monitored by the PPD to the hat module and receive the control command signal from the hat module.

11. The NEI device of claim 10, wherein the power and signal processor comprises a synchronous sample/hold (SSH) module configured to transform an analog signal output from the PPD into a digital signal and transmit the digital signal to the DBMS communicator.

12. The NEI device of claim 10, wherein power output from the power modulator is a pulse wave which has a magnitude between 0V and +10V, a frequency of 200 Hz or more, and a pulse width between 60 psec and 500 psec.

13. The NEI device of claim 1, wherein the hat module comprises:
a power transmitter configured to wirelessly transmit the power to the DBMS module;
a communicator configured to perform a wireless communication with the DBMS module; and
a remote controller configured to control a power transmission function of the power transmitter, and analyze and process a monitoring signal transmitted from the communicator to transmit a command signal to control a cerebral nerve stimulation function of the DBMS module through the communicator.

14. The NEI device of claim 13, wherein if the monitoring signal has a shock waveform or abruptly fluctuates, the remote controller is configured to control the power transmitter to increase wireless power transmitted to the DBMS module.

15. The NEI device of claim 13, wherein if the monitoring signal corresponds to a signal type written in a lookup table, the remote controller controls the power transmitter to increase the wireless power transmitted to the DBMS module using the lookup table, wherein abnormal signal types are written in the lookup table through an experiment.

16. The NEI device of claim 13, wherein the remote controller is configured to transmit a command signal to control a monitoring period to the DBMS module through the communicator according to the monitoring signal.

* * * * *